(12) United States Patent
Fischer et al.

(10) Patent No.: US 9,717,661 B2
(45) Date of Patent: Aug. 1, 2017

(54) METHODS FOR CLEANING AND REMINERALIZING TEETH

(71) Applicant: ULTRADENT PRODUCTS, INC., South Jordan, UT (US)

(72) Inventors: Dan E. Fischer, Sandy, UT (US); Peter M. Allred, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 14/883,462

(22) Filed: Oct. 14, 2015

(65) Prior Publication Data
US 2016/0030308 A1 Feb. 4, 2016

Related U.S. Application Data (62) Division of application No. 12/182,892, filed on Jul. 30, 2008, now Pat. No. 9,226,895.

(51) Int. Cl.
| | | |
|---|---|---|
| *A61K 8/21* | (2006.01) | |
| *A61K 8/22* | (2006.01) | |
| *A61K 8/24* | (2006.01) | |
| *A61Q 11/00* | (2006.01) | |
| *A61K 33/06* | (2006.01) | |
| *A61K 9/68* | (2006.01) | |
| *A61K 8/42* | (2006.01) | |

(52) U.S. Cl.
CPC .......... *A61K 8/22* (2013.01); *A61K 8/21* (2013.01); *A61K 8/42* (2013.01); *A61K 9/0058* (2013.01); *A61Q 11/00* (2013.01); *A61K 2800/88* (2013.01); *A61K 2800/884* (2013.01)

(58) Field of Classification Search
USPC ........................ 424/57, 53, 52, 49
See application file for complete search history.

(56) References Cited

U.S. PATENT DOCUMENTS

| | | |
|---|---|---|
| 4,083,955 A | 4/1978 | Grabenstetter et al. |
| 4,177,258 A | 12/1979 | Gaffar et al. |
| 4,183,915 A | 1/1980 | Gaffar et al. |
| 4,348,381 A | 9/1982 | Gaffar et al. |
| 4,397,837 A | 8/1983 | Raaf et al. |
| 5,372,802 A | 12/1994 | Barrows et al. |
| 6,120,754 A | 9/2000 | Lee et al. |
| 6,365,134 B1 | 4/2002 | Orlowski et al. |
| 6,497,858 B1 | 12/2002 | Takatsuka et al. |
| 2005/0281759 A1 | 12/2005 | Tung |
| 2006/0110340 A1* | 5/2006 | Tung .............. A61K 8/19 424/53 |

FOREIGN PATENT DOCUMENTS

| | | |
|---|---|---|
| JP | 2004210722 | 7/2004 |
| JP | 2005112841 | 4/2005 |

OTHER PUBLICATIONS

Rodrigues, J. et al., "Effects of 10% carbamide peroxide bleaching materials on enamel microhardness", Research Article, C.E. Article #7-201, American Journal of Dentistry, vol. 14, No. 2, Apr. 2001.
American Dental Association, "New Tooth Whitener Could Help Heal Teeth", The Tooth of the Matter, p. 3, at least as early as Oct. 17, 2005.
Halford, "Materials Science Blossoms in Boston, Talks feature tooth whitening, electrochronic plastics, smart textiles, and nanoaprticle studies", Science & Technology, pp. 49-50, Dec. 19, 2005.
U.S. Appl. No. 12/182,892, Mar. 3, 2011, Office Action.
U.S. Appl. No. 12/182,892, Aug. 17, 2011, Office Action.
U.S. Appl. No. 12/182,892, May 12, 2014, Office Action.
U.S. Appl. No. 12/182,892, Dec. 5, 2014, Office Action.
U.S. Appl. No. 12/182,892, Sep. 28, 2015, Notice of Allowance.

* cited by examiner

*Primary Examiner* — Lezah Roberts
(74) *Attorney, Agent, or Firm* — Workman Nydegger (57) ABSTRACT

Methods for use in selectively conditioning and remineralizing teeth. An exemplary method comprises the steps of applying a conditioning composition to one or more of a person's teeth, and separately applying a remineralizing composition to the person's teeth. The conditioning composition includes a conditioning agent, and the remineralizing composition includes a remineralizing agent comprising calcium ions and/or fluoride ions. The conditioning composition may be applied prior to or after application of the remineralizing composition. In one embodiment, both the conditioning composition and the remineralizing composition include different remineralizing ions (e.g., one including calcium, one including fluoride).

20 Claims, 7 Drawing Sheets

METHODS FOR CLEANING AND REMINERALIZING TEETH

CROSS REFERENCE TO RELATED APPLICATION

This application is a division of U.S. patent application Ser. No. 12/182,892, filed Jul. 30, 2008, the disclosure of which is incorporated herein in its entirety.

BACKGROUND OF THE INVENTION

1. The Field of the Invention

The present invention is in the field of compositions, kits, and methods for cleaning and remineralizing a person's teeth.

2. The Relevant Technology

Virtually all people desire white or whiter teeth. To achieve this goal, people often have their teeth chemically bleached, which has become very popular in recent years. Even so, bleaching with peroxides (a typical active bleaching agent within a bleaching composition) has been shown to affect the surface morphology of enamel. In addition, studies are now showing that bleaching can have a negative impact on the micro and nano hardness of enamel. Both of these effects are believed to be caused by demineralization of the enamel during the tooth whitening process. Studies have also shown however, that the condition of the enamel typically improves to a condition near what it was before the bleaching treatment within a couple of weeks after bleaching has ended. It is believed that this occurs because the natural oral environment provides fluoride, calcium, and other mineral ions which allow this recovery to occur.

Although improvement seems to occur in typical cases, there is no guarantee that all of the necessary materials and/or ions are present in any particular person's saliva during this repair time. For example, there may be other materials and/or ions present in the saliva that might interfere and cause some randomization to the repair. Furthermore, the extent of improvement of any given individual may vary based on dietary differences, mineral concentrations in drinking water, whether the person smokes, or other factors affecting the environment within the mouth and the concentrations of components within the person's saliva. In addition, during the time in which the enamel surface is weakened and before repair can occur naturally, deterioration to the enamel surface may be more likely to occur as a result of bacteria and other microbes present within the oral cavity.

Other treatments (e.g., orthodontic procedures) are also known to result in demineralization and weakening of the enamel of a patient's teeth. In the case of orthodontic treatments, it is often difficult to thoroughly brush, floss, and otherwise care for the teeth and gum tissue while orthodontic appliances are in place. In addition, orthodontic brackets necessarily cover a portion of the tooth enamel as they are bonded to the tooth surface for several months or longer (e.g., sometimes years), making care of the underlying and surrounding enamel and other tissues very difficult. As a result, demineralization and weakening of the enamel is often an undesirable side effect of orthodontic treatment.

BRIEF SUMMARY OF THE INVENTION

The present invention is directed to methods and associated kits for use in selectively conditioning and remineralizing teeth. The inventive method comprises the steps of applying a conditioning composition to one or more of a person's teeth, and applying a remineralizing composition to the person's teeth. The compositions are applied within about 1 hour of one another so as to optimize results achieved by the method. Preferably, the compositions are applied within about 30 minutes of one another, more preferably within about 10 minutes of one another, and most preferably the application of the second composition is immediately subsequent to application of the first composition. In other words, preferably, there is little or no passage of time between removal of the first composition (e.g., spitting out a rinse, a paste, a gum, or removing a tray used to hold a gel against the teeth), and placement of the second composition within the mouth against the teeth. The conditioning composition may be applied prior to or after the application of the remineralizing composition. The conditioning composition includes a conditioning agent, for example, a peroxide component configured to clean and prepare the enamel and/or dentin tooth exterior surface for remineralization. At least the remineralizing composition advantageously includes a remineralizing ion comprising at least one of calcium or fluoride. In one preferred embodiment, both the conditioning composition and the remineralizing composition include remineralizing ions. For example, the conditioning composition may include calcium ions, and the remineralizing composition may include fluoride ions.

An exemplary related kit includes both a conditioning composition and a remineralizing composition. The conditioning composition includes a conditioning agent, which may comprise a peroxide conditioning agent. Such peroxide conditioning agents act to condition and prepare the tooth enamel by cleaning and temporarily weakening the crystalline surface in preparation for remineralizing the surface with specifically selected ions. As a practical matter, both the remineralizing and conditioning compositions include one or more solvents or carriers to aid in application and delivery of the conditioning and remineralizing agents, respectively, to the enamel and/or dentin surfaces. The inventive kit and method allow for selective and intentional conditioning and remineralizing of tooth tissues through the related two step method. For example, the kit and method may be used for selective application to enamel and/or exposed dentin tissue weakened during orthodontic treatment or tooth whitening so as to strengthen and remineralize the enamel. Such strengthening and remineralization is accomplished faster and with higher concentrations of preferred remineralization ions (with improved strength and decay resistance), as the concentration and types of remineralization ions present within the oral cavity may be carefully controlled.

Such kits and methods allow a user or practitioner to selectively condition and remineralize teeth with much more control over how and when remineralization occurs. In other words, rather than waiting for the natural concentration of remineralizing components within the patent's saliva to effect remineralization and repair (which may or may not occur for any particular patient), the provided kit and method may be used to intentionally and selectively condition and then immediately remineralize and repair the tooth enamel and/or exposed dentin. Such methods and kits may substantially speed up repair and remineralization of enamel and/or dentin, as the surfaces are prepared to receive needed ions, and concentrations of desired ions are actively provided, rather than relying on saliva and diet alone for their presence. In addition, by controlling the types and concentrations of ions provided during the conditioning and subsequent remineralization, the kit and method is believed to provide for improved enamel strength relative to a scenario in which remineralization occurs naturally. Such methods and kits are useful for selective conditioning and repair so as to improve tooth enamel structure and hardness during and/or after orthodontic treatment, dental bleaching, or other instances where enamel and/or dentin health is known to deteriorate.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention is directed to methods and kits for use in selectively conditioning and remineralizing teeth. The inventive kit includes both a conditioning composition and a remineralizing composition. The conditioning composition acts to prime, prepare, clean, and condition the enamel surface in preparation for repair and remineralization of the enamel structure. The conditioning composition includes a conditioning agent (e.g., a peroxide) which acts to prime, clean, and prepare the enamel surface in preparation for remineralization in a controlled manner. Although the conditioning step temporarily weakens the enamel surface, the methods and kits immediately (or nearly so) provide available remineralization ions to subsequently strengthen the surface. The remineralizing composition advantageously includes a remineralizing ion comprising at least one of calcium or fluoride. The remineralizing ion is present and available (e.g., soluble in saliva) at a sufficient concentration to provide available ions to remineralize the enamel in a controlled manner. The kit and method advantageously allow a dental practitioner to identify a patient with weakened and/or demineralized enamel or exposed dentin and to selectively apply the compositions so as to repair, strengthen, and remineralize the affected tooth surfaces.

The compositions are applied within about 1 hour of one another so as to optimize results achieved by the method. Preferably, the compositions are applied within about 30 minutes of one another, more preferably within about 10 minutes of one another, and most preferably the application of the second composition is immediately subsequent to application of the first composition. Reduction of the amount of time between removal of one composition and application of the second composition reduces the time in which rogue ions present within the oral cavity can interfere with the remineralization treatment. In addition, reducing any lag time between removal of the first applied composition and application of the second composition better utilizes the elevated ion concentrations present within the oral cavity immediately subsequent to application of the first composition. In other words, preferably, there is little or no passage of time between removal of the first composition (e.g., spitting out a rinse, a paste, a gum, or removing a tray used to hold a gel against the teeth), and placement of the second composition within the mouth against the teeth.

II. Exemplary Kits and Methods

Figure 1:
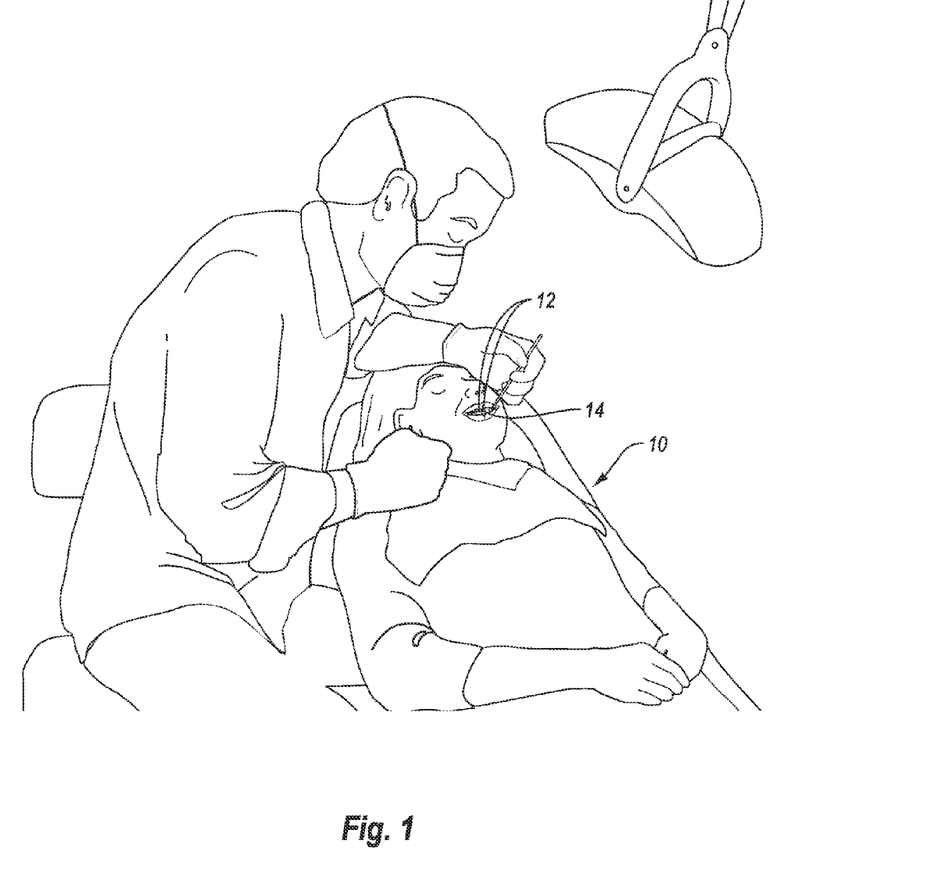
FIG. 1 illustrates a patient having completed orthodontic treatment in which the orthodontic brackets and arch wire are being removed from the teeth.
Figure 2:
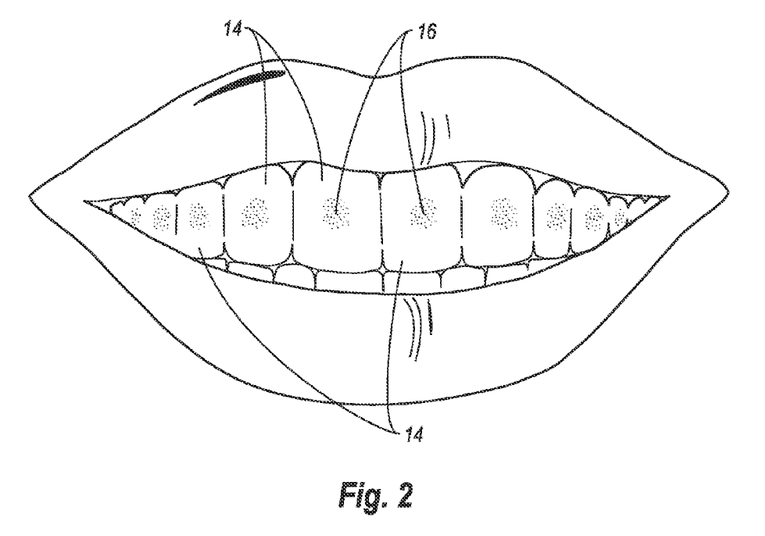
FIG. 2 illustrates the patient of FIG. 1 after all orthodontic brackets have been removed from the teeth and in which the teeth include demineralized regions where the brackets were bonded.

FIGS. 1 and 2 illustrate a patient 10 having just completed an orthodontic treatment and in which the orthodontic brackets 12 are being removed from the teeth 14. As shown, there is typically an area of demineralized and/or weakened enamel 16 where the bracket was bonded to each tooth 14. Similar weakening and demineralization of the enamel is typical following a tooth whitening treatment in which the teeth are exposed to concentrated peroxide dental bleaching agents and/or over a prolonged time period. Such weakened enamel surfaces can be repaired by means of kits and methods according to the present invention.

Figure 3A:
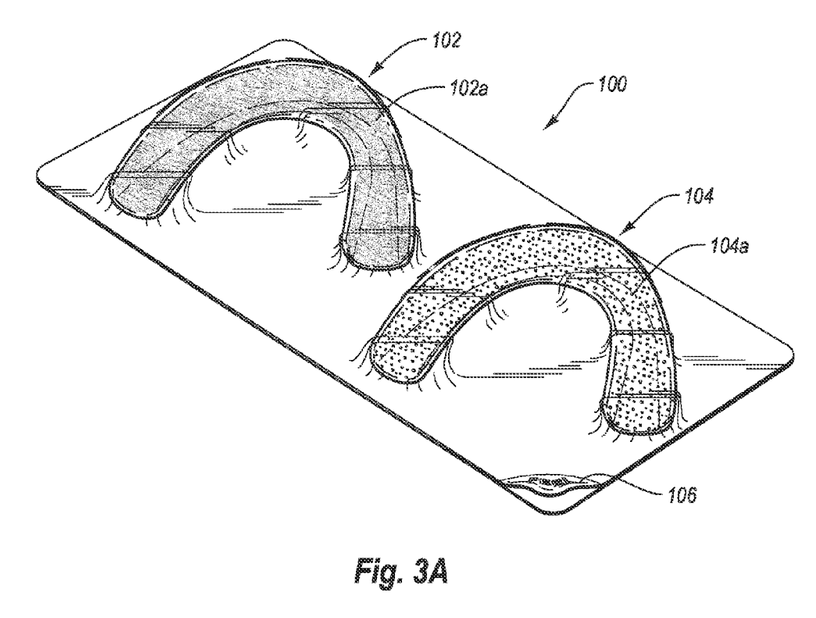
FIG. 3A is a perspective view of an exemplary kit including a conditioning composition formulated as a gel and a remineralizing composition also formulated as a gel, in which the gels are disposed adjacent to respective tray shaped barrier layers.

FIG. 3A illustrates an exemplary kit 100 including a first tray shaped barrier layer including a conditioning composition 102a preloaded within the tray 102. Kit 100 also includes a second tray shaped barrier layer 104 including a remineralizing composition 104a preloaded within tray 104. The trays 102 and 104 are illustrated as packaged within a covered container with a peelable cover layer 106, which serves to protect the compositions prior to use. In order to use such a kit, the user may peel away cover 106 and position tray 102 against the dental arch of the teeth to be treated. Afterwards, the tray 104 is positioned over one of the person's dental arch to expose the person's teeth to the remineralizing composition 104a. The kit may include one or more additional trays so as to provide trays for both the upper and lower dental arches (or to provide for multiple treatments). Although kit 100 is illustrated with the compositions 102a and 104a preloaded within the trays, alternatively each composition may be initially contained within a container (e.g., a syringe), from which the user dispenses the composition just prior to application to the teeth.

According to one method, the gel conditioning and gel remineralizing compositions may typically be maintained in place for about 10 minutes to about 12 hours. The treatment time may be adjusted, depending particularly on the format of the conditioning and remineralizing compositions. For example, gel compositions may be formulated by varying the fraction of the conditioning and remineralizing components, as well as the other components, so as to provide the desired results when the gel is maintained in place for about 10 minutes to about 12 hours. With other formats (e.g., rinses or pastes), it may be desirable to increase fractions of the conditioning and remineralizing components so as to provide a desired treatment in less time (e.g., within about 30 seconds to about 2 minutes of rinsing or brushing).

By way of example, not limitation, a typical gel conditioning or remineralizing session of fast duration (e.g., employing higher concentrations of conditioning and remineralizing agents, respectively) may last from about 10 to about 30 minutes; a conditioning or remineralizing session of intermediate duration may last from about 30 minutes to about 2 hours; and a conditioning or remineralizing session of long duration, including overnight wearing of a gel filled tray while a person is sleeping, may last from about 2 hours to about 12 hours. Alternatively, rather than increasing the fraction of conditioning or remineralizing agents within the gels or other format compositions, the conditioning and remineralizing regimen may depend on repeating exposure so as to increase exposure to the conditioning and remineralizing agents. For example, a method may involve repeating application of a conditioning gel once a day for several days (e.g., about a week), followed by application of a remineralizing gel once a day for several days (e.g., about a week).

Conditioning composition 102a is able to condition tooth enamel and/or exposed dentin as a preliminary step to remineralization. Conditioning composition 102a includes at least one conditioning agent which acts to clean and prepare the surface so that it will more readily accept calcium and fluoride ions to be applied. One currently preferred example of a conditioning agent is a peroxide, such as are commonly used in dental bleaching. Examples of peroxide conditioning agents include aqueous hydrogen peroxide, carbamide peroxide, metal perborates (e.g., sodium perborate), metal percarbonates (e.g., sodium percarbonate), metal peroxides (e.g., calcium peroxide), metal chlorites and hypochlorites, peroxy acids (e.g., peroxyacetic acid), and peroxy acid salts. Because of the peroxide conditioning agent, the conditioning compositions are typically acidic (i.e., having a pH less than 7), having a pH preferably between about 4 and about 7, more preferably between about 4 and about 5. pH values less than about 3 are much less preferred, as such highly acidic compositions tend to destroy the surface enamel in an accelerated manner rather than more mildly cleaning and conditioning the surface, as desired.

One side benefit associated with the peroxide conditioning agent is that the conditioning composition may act to whiten the enamel at the same time it is being cleaned and conditioned in preparation for remineralization, although this is not the primary purpose of the conditioning treatment. As such, the fraction of peroxide conditioning agent within the conditioning compositions may be significantly less than that provided in similar dental bleaching compositions. For example, such compositions may include relatively small amounts of peroxide conditioning agents (e.g., greater than 0% to less than about 1%, for example, about 0.5% by weight of the conditioning composition). However more preferred conditioning compositions may include a peroxide conditioning agent that comprises between about 1% to about 60% by weight of the conditioning composition, more preferably in a range of about 5% to about 40% by weight, and most preferably in a range of about 10% to about 30% by weight. In addition to the format of the composition, the exact fraction selected may depend on the particular peroxide bleaching agent selected. For example, aqueous hydrogen peroxide is much more potent (e.g., about 3 times more) than other forms of peroxides, and as such, less is required to achieve a similar result.

In one embodiment, the conditioning composition may comprise a peroxide containing dental bleaching composition. Existing peroxide dental bleaching compositions may optionally be modified by addition of a small amount of a remineralizing agent (e.g., a soluble fluoride salt or calcium salt) so as to provide a conditioning composition containing available remineralizing ions. Exemplary peroxide dental bleaching compositions that may be used as conditioning compositions are disclosed in U.S. Pat. No. 5,376,006; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat. No. 6,500,408; U.S. Pat. No. 6,503,485 and U.S. patent application Ser. No. 11/460,016 filed Jul. 26, 2006. For purposes of disclosing peroxide conditioning compositions, and methods of making such compositions, the foregoing patents and application are incorporated herein by reference. The conditioning compositions may be formulated as a gel, a rinse, a paste, or as a solid chewable gum, similar to the consistency of chewing gum. Other formats may be apparent to one skilled in the art.

The remineralizing composition includes at least a remineralizing agent comprising a remineralizing ion. Exemplary additional optional components that may be included in either the conditioning composition, the remineralizing composition, or both, include solvents or carrier components, thickeners, sweeteners, flavorants, colorants, pH buffers, pH neutralizers, surfactants, humectants, abrasives, desensitizers (e.g., potassium nitrate), and preservatives.

Although each remineralizing composition in FIGS. 3A-3D is illustrated as being pre-loaded (e.g., as a gel) within a tray shaped barrier layer, it is to be understood that the remineralizing compositions may likewise be formulated so as to have any desired consistency and/or format (e.g., as a gel, a rinse, a paste, or as a solid chewable gum, similar to the consistency of chewing gum). In addition to the remineralizing ions provided by the remineralizing composition, the conditioning composition may optionally include a remineralizing ion (e.g., different from that provided by the remineralizing composition).

Exemplary remineralizing agents include various calcium and/or fluoride containing materials which provide calcium and/or fluoride ions that are available (e.g., soluble in the saliva) for remineralization of the enamel and/or exposed dentin tissue. Exemplary remineralizing agents include calcium and fluoride compounds including, but not limited to, calcium phosphate monobasic, calcium phosphate dibasic, anhydrous calcium phosphate, and sodium fluoride. The above remineralizing agents provide available remineralizing ions when present within the oral cavity environment (e.g., calcium ions or fluoride ions become soluble within the saliva and/or water present within the composition and/or oral cavity). The remineralizing agents preferably collectively comprise between about 2 percent and about 20 percent by weight of the remineralizing composition, more preferably between about 3 percent and about 15 percent by weight of the composition, and most preferably between about 5 percent and about 12 percent by weight of the composition.

Preferably, the remineralizing agent of the remineralizing composition comprises at least calcium ions. In some embodiments, fluoride remineralizing agents may also be included within the remineralizing composition (preferably in small amounts, most preferably between about 0.1 percent and about 3 percent by weight). In embodiments where the remineralizing composition includes calcium remineralizing ions, the accompanying conditioning composition may advantageously include remineralizing fluoride ions (e.g., through inclusion of a fluoride salt such as sodium fluoride). Such conditioning compositions preferably include between about 0.1 percent and about 3 percent by weight of a remineralizing agent containing fluoride, more preferably between about 0.15 percent and about 1 percent by weight, and most preferably between about 0.2 percent and about 0.5 percent by weight (e.g., about 0.25 percent). One particularly preferred kit may provide a conditioning composition including a peroxide conditioning agent as well as remineralizing ions consisting of fluoride (i.e., no calcium is included), and a remineralizing composition that separately includes the calcium remineralizing ions. The remineralizing composition may also include additional fluoride ions.

Suitable solvents or carriers for use in either conditioning or remineralizing compositions, particularly for compositions having the consistency of a rinse, gel, or paste include, but are not limited to, ethyl alcohol, water, propylene glycol, glycerine, and polyethylene glycol. Chewable gum compositions may include gum base, wax free gum base, and/or polyvinyl acetate as carrier and/or thickener components. Exemplary thickeners (e.g., in gel, paste, or chewing gum compositions) include, but are not limited to, carboxymethylcellulose, carbopol, gum base, wax free gum base, polyvinyl acetate, fumed silica, and/or polyvinylpyrollidone. Preservatives, pH buffers, pH neutralizers, sweeteners, flavorants, colorants, surfactants, humectants, abrasives, desensitizers, and other components may be added, as desired.

Perhaps counter-intuitively, the conditioning composition acts to preliminarily weaken and demineralize the exterior enamel and/or dentin tooth surface to which it is applied. It is believed that first weakening and demineralizing the enamel prepares the enamel surface for exposure to the remineralizing ions of the remineralizing composition by opening channels within the enamel surface into which the remineralizing calcium and fluoride ions can then penetrate and bond, recrystallizing the enamel or dentin structure to a configuration that is stronger than it was before the treatment. In this way, the practitioner or other user is able to control the degree of the conditioning step, the concentration of selected remineralizing ions such as calcium and fluoride used for enamel strengthening and repair, as well as the amount of time that the conditioned enamel is exposed to the remineralizing composition. As such, the user is able to repair and strengthen enamel that may deliberately be in a weakened, demineralized state (e.g., as a result of orthodontic treatment). Such treatments may even be helpful to improve the strength and mineralization of otherwise healthy enamel to a level greater than it was before the treatment. In other words, the method and kit is useful both for improving already relatively healthy enamel and in strengthening and remineralizing enamel and/or surface dentin presently in a weakened state as a result of some earlier treatment.

Figure 3B:
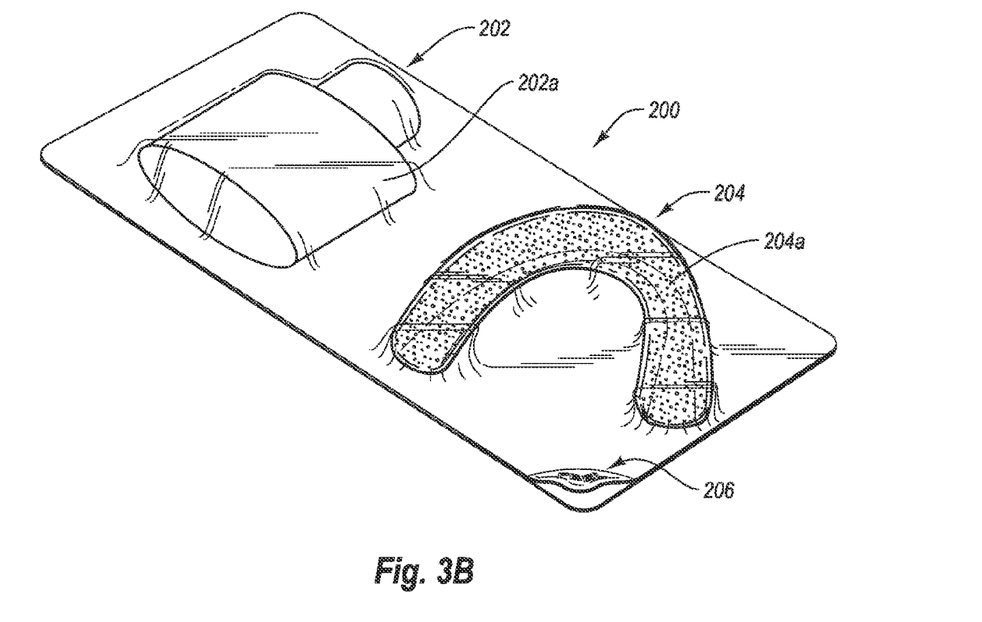
FIG. 3B is a perspective view of an exemplary kit including a conditioning composition formulated as a rinse disposed within a container disposed adjacent a tray shaped barrier layer pre-loaded with a remineralizing composition formulated as a gel.

FIG. 3B illustrates an exemplary kit 200 including a container (e.g., a bottle) 202 containing a conditioning composition 202a. For ease of application from bottle 202, composition 202a may be formulated as a rinse. Formulating conditioning composition 202a as a rinse may also be preferred by some users, as a rinse may be easily applied (e.g., similar to a mouthwash) so as to prepare tooth enamel and/or dentin for remineralization. As a practical matter, exposure times for a rinse may be shorter than those employed when using a gel (e.g., about 30 seconds to about 2 minutes as compared to about 10 minutes to about 12 hours). As such, it may be desirable to include the conditioning agent in higher concentration as compared to a gel conditioning composition intended for longer exposure.

Kit 200 also includes a tray shaped barrier layer 204 including a remineralizing composition 204a preloaded within tray 204. Composition 204a may advantageously be formulated as a gel. The container 202 and tray 204 are illustrated as packaged within a covered container with a peelable cover layer 206, which serves to protect at least the gel composition 204a prior to use. In order to use such a kit, the user may peel away cover 206, apply rinse composition 202a from container 202 to the person's teeth, for example by rinsing the composition within the person's mouth for a suitable period (e.g., about 30 seconds to about 2 minutes). Afterwards, the tray 204 is positioned over one of the person's dental arch to expose the person's teeth to the remineralizing composition 204a. The gel remineralizing composition may typically be maintained in place for about 10 minutes to about 12 hours. The kit may include an additional tray so as to provide trays for both the upper and lower dental arches, or to provide for additional remineralization treatments. If desired, additional remineralizing trays 204 may be subsequently applied so as to strength the enamel and/or dentin to a desired level.

Figure 3C:
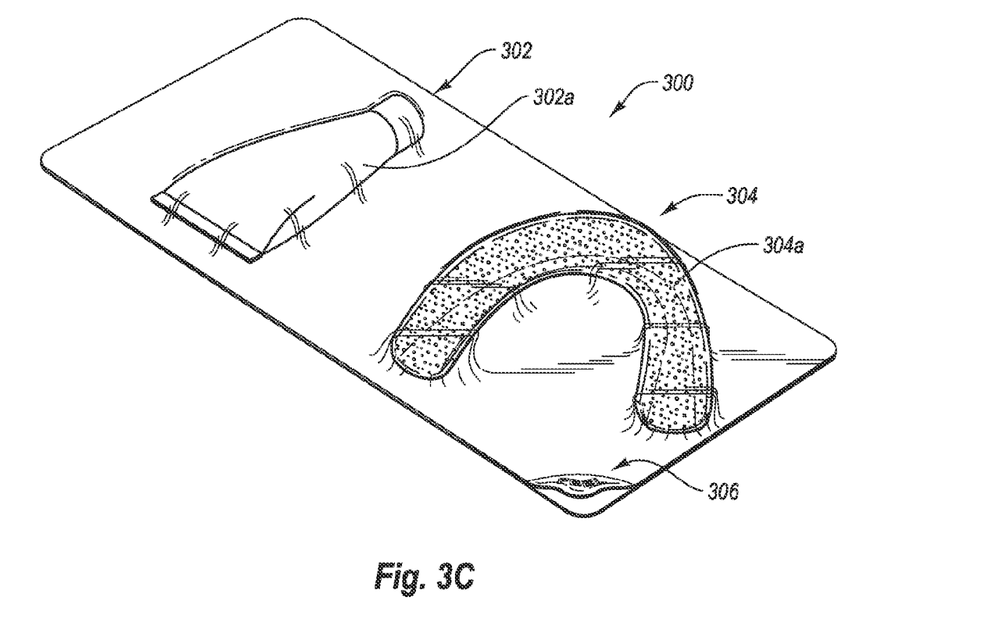
FIG. 3C is a perspective view of an exemplary kit including a conditioning composition formulated as a paste contained within a tube disposed adjacent a tray shaped barrier layer pre-loaded with a remineralizing composition formulated as a gel.

FIG. 3C illustrates another exemplary kit 300 including a container (e.g., tube) 302 containing a conditioning composition 302a in the form of a paste. For ease of application container 302 may be configured as a squeezable tube 302. Kit 300 also includes a tray shaped barrier layer 304 including a remineralizing composition 304a preloaded within tray 304. Composition 304a may advantageously be formulated as a gel. The container 302 and tray 304 are illustrated as packaged within a covered container with a peelable cover layer 306, which serves to protect at least the gel composition 304a prior to use. In order to use such a kit, the user may peel away cover 306, apply paste composition 302a from container 302 to the person's teeth, for example by brushing the composition onto the person's teeth for a suitable period (e.g., about 30 seconds to about 2 minutes). Afterwards, the tray 304 is positioned over one of the person's dental arch to expose the person's teeth to the remineralizing composition 304a. The gel remineralizing composition may typically be maintained in place for about 10 minutes to about 12 hours. The kit may include an additional tray so as to provide trays for both the upper and lower dental arches, or to provide for additional remineralization treatments. If desired, additional remineralizing trays 304 may be subsequently applied so as to strength the enamel and/or dentin to a desired level.

Figure 3D:
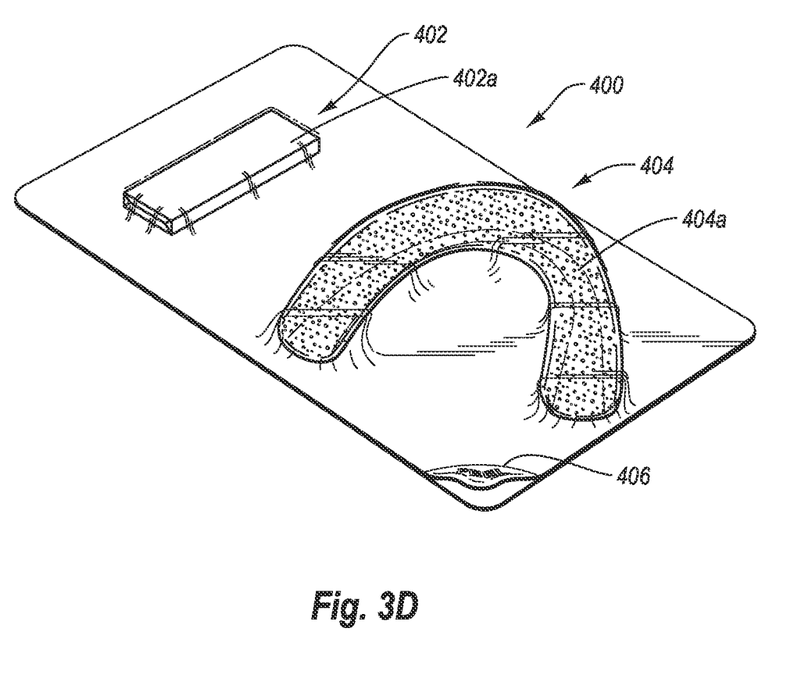
FIG. 3D is a perspective view of an exemplary kit including a conditioning composition formulated as a chewable gum packaged adjacent a tray shaped barrier layer pre-loaded with a remineralizing composition formulated as a gel.

FIG. 3D illustrates an exemplary kit 400 including a container (e.g., a package) 402 containing a conditioning composition 402a. Package 402 may be formulated as a chewable gum. Kit 400 also includes a tray shaped barrier layer 404 including a remineralizing composition 404a preloaded within tray 404. Composition 404a may advantageously be formulated as a gel. The package 402 and tray 404 are illustrated as packaged within a covered container with a peelable cover layer 406, which serves to protect at least the gel composition 404a prior to use. In order to use such a kit, the user may peel away cover 406, remove chewing gum composition 402a from package 402, and chew the gum for a suitable period (e.g., about 1 minute to about 30 minutes). Afterwards, the tray 404 is positioned over one of the person's dental arch to expose the person's teeth to the remineralizing composition 404a. The gel remineralizing composition may typically be maintained in place for about 10 minutes to about 12 hours. The kit may include an additional tray so as to provide trays for both the upper and lower dental arches, or to provide for additional remineralization treatments. If desired, additional remineralizing trays 404 may be subsequently applied so as to strength the enamel and/or dentin to a desired level.

Because the methods and kits rely on first conditioning the enamel and/or exposed dentin surface prior to remineralization, it is preferred that the conditioning composition be applied prior to application of the remineralizing composition. It is, however, possible to first apply the remineralizing composition, as it is believed that the remineralizing ions provided by the composition will provide an elevated concentration of remineralizing ions within the oral cavity that may remain elevated for a significant period of time so as to provide available remineralizing ions once the surface has been conditioned. As such, it may be possible to apply the remineralizing composition first, followed by application of the conditioning composition. Once the conditioning composition is applied, it is believed that the residual remineralizing ions of the remineralizing composition present within the saliva will then be attracted to the conditioned enamel and/or exposed dentin surface, resulting in remineralization.

In another method and related kit, a conditioning composition (e.g., a gel) is first applied to the teeth to be conditioned for remineralization, after which a remineralization composition (e.g., in the form of a gel) is applied to the conditioned teeth. In order to even more fully remineralize the teeth, the first remineralizing gel composition may be followed by a second remineralizing composition in a form different from the first remineralizing composition that would be more acceptable to the user (e.g., a chewable gum). For example, a gel remineralizing composition may be followed by application of additional remineralizing composition in the form of a chewable gum. Such a conditioning gel, remineralizing gel, and chewing gum application is particularly preferred as the gel applications may result in higher exposure to conditioning and remineralizing agents over a relatively short time period, while the chewing gum application is more convenient to the person being treated. As such, the gels may be used to achieve the conditioning step and most of the remineralization step, after which the chewing gum remineralizing composition acts to provide additional remineralizing ions over a longer, more extended time period with a minimum of discomfort and/or hassle to the user. For example, the user may chew such a gum composition one or more times a day for several days (e.g., about a week) to complete the treatment.

Figure 4:
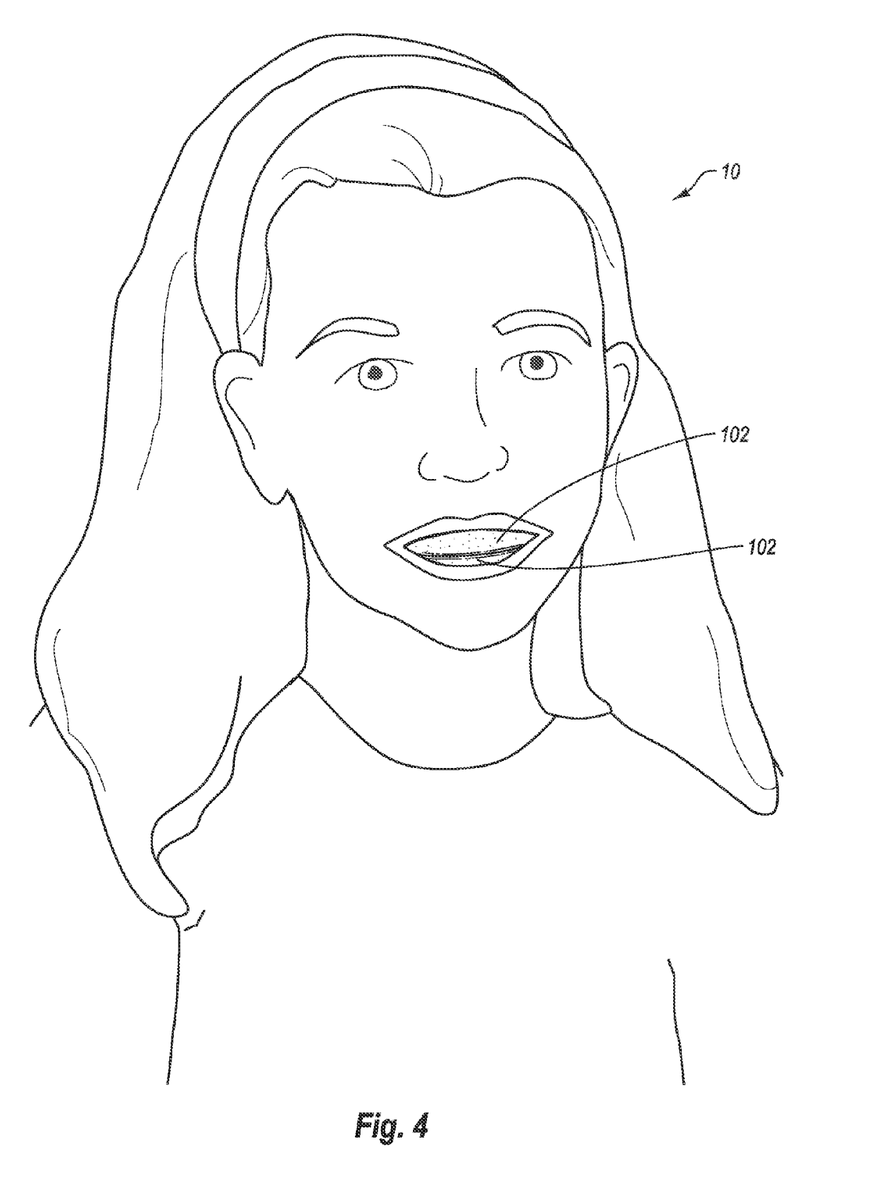
FIG. 4 is a perspective view of the patient of FIG. 1 having placed a conditioning composition disposed within a tray shaped barrier layer over her teeth.
Figure 5:
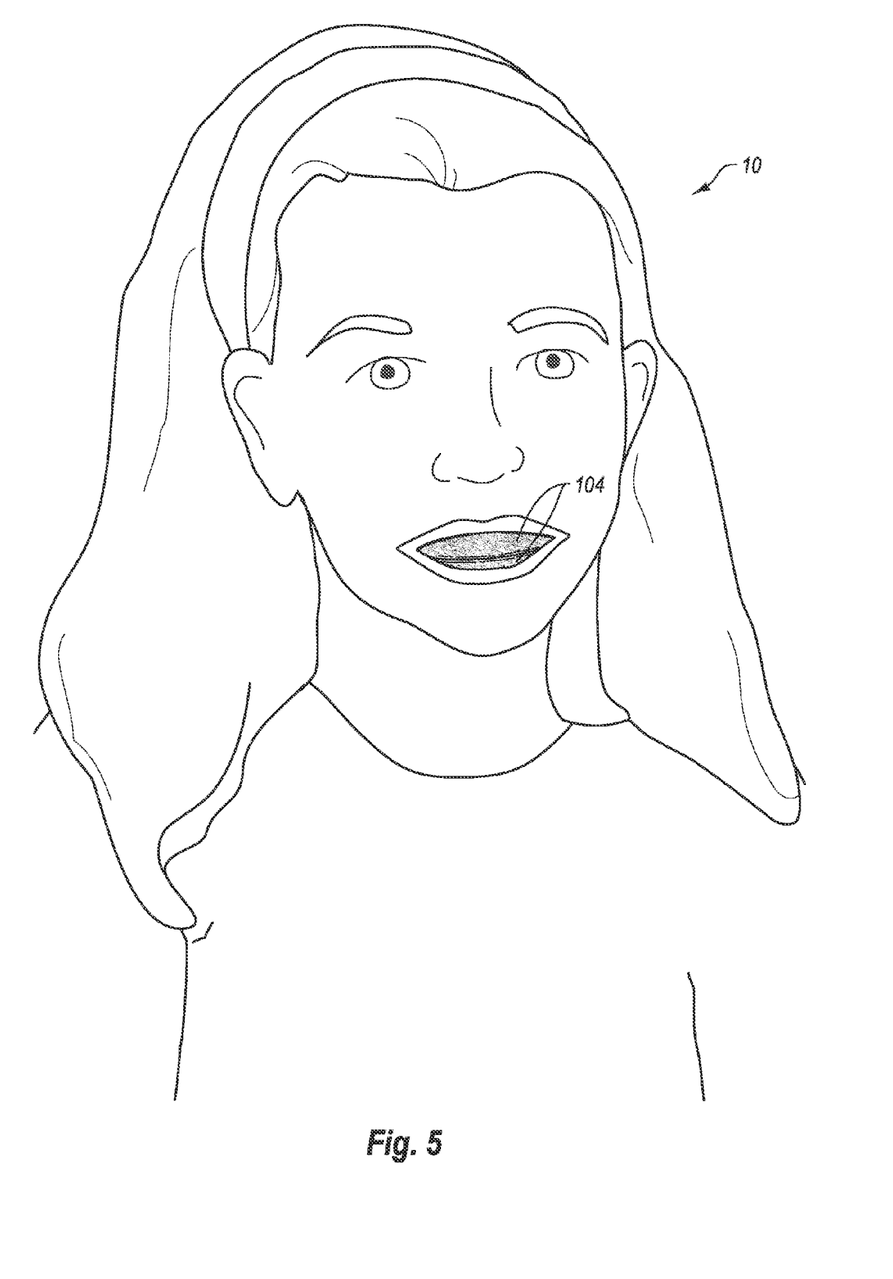
FIG. 5 is a perspective view of the patient of FIG. 4 after having removing the conditioning trays and having placed a remineralizing composition disposed within a tray shaped barrier layer over her teeth.
Figure 6:
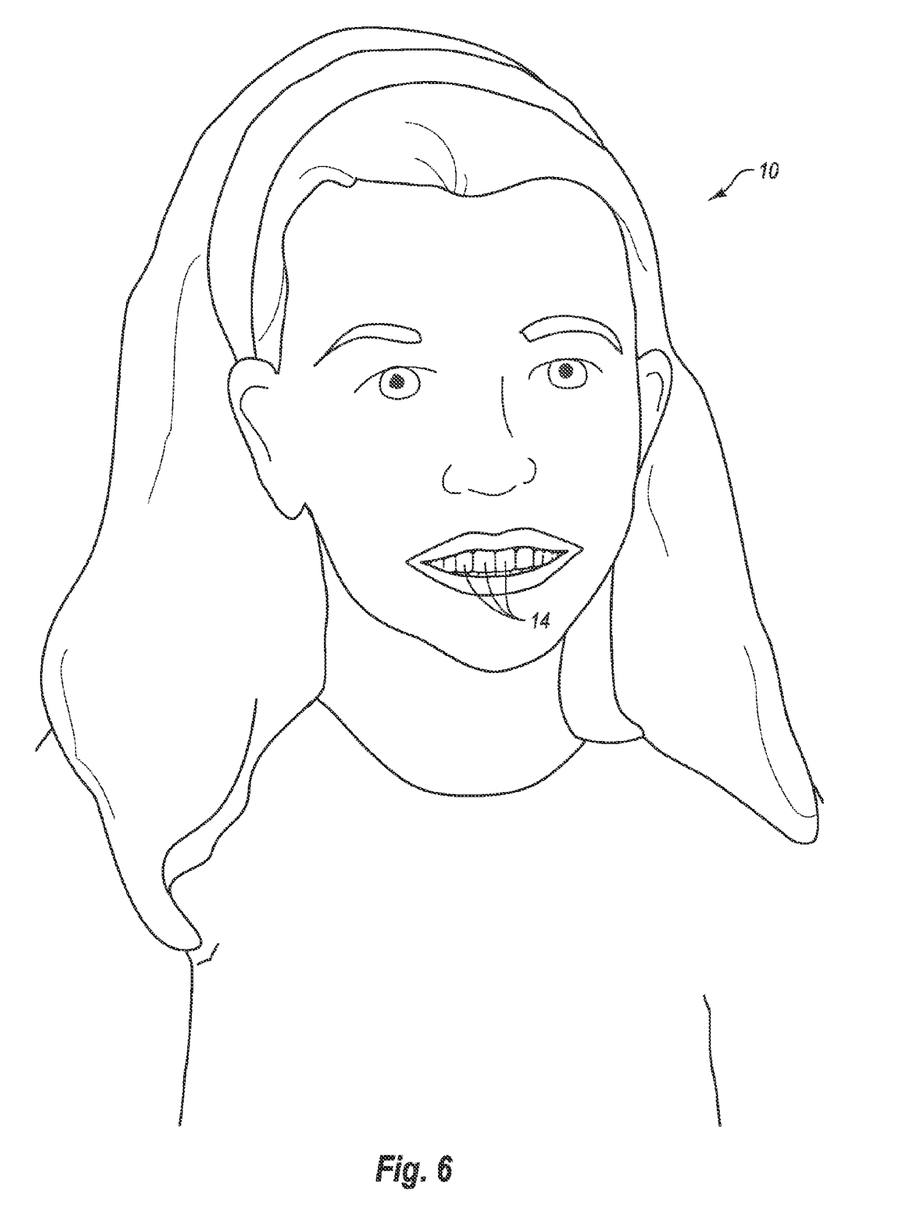
FIG. 6 is a perspective view of the patient of FIG. 5 once the remineralizing composition and tray-shaped barrier layer have been removed and in which the patient's tooth enamel has been remineralized.

FIG. 4 illustrates an exemplary method of use in which conditioning tray 102 containing a conditioning composition (e.g., formulated as a gel) is placed adjacent the upper and lower dental arches of user 10 in order to condition the enamel and/or exposed dentin surface preparatory to application of a remineralizing composition. As shown in FIG. 5, once the conditioning trays 102 have been in place for a sufficient time (e.g., about 10 minutes to about 12 hours), the user removes the conditioning trays 102, and places remineralizing trays 104 over the upper and lower dental arches. The user may remove residual conditioning composition prior to placing the remineralizing trays, although this is not necessary, and may actually be somewhat advantageous, particularly where the conditioning composition also includes remineralizing ions. The remineralizing trays are left in place for a suitable treatment time (e.g., about 10 minutes to about 12 hours), after which the trays may be removed and any remaining conditioning and/or remineralizing composition may be brushed and/or rinsed from the person's teeth. As described above, the conditioning trays 104 may be followed by a period in which additional remineralizing composition is applied in the form of a chewable gum. As shown in FIG. 6, once the treatment is complete the exterior tooth surfaces (e.g., enamel and/or exposed dentin) are remineralized, reversing the demineralization previously present as shown in FIG. 1.

III. EXAMPLES

Example 1

A sticky, viscous conditioning gel composition was prepared by mixing together the following components:

| | | |
|---|---|---|
| Water | 22.5% | solvent/carrier |
| EDTA Disodium | 0.1% | pH buffer |
| Carbamide Peroxide | 18.5% | conditioning agent |
| Sucralose 25% solution | 0.75% | sweetener/flavorant |
| Glycerine | 41.6% | solvent/carrier |
| Carbopol 974 | 5.3% | thickener |
| Sodium Hydroxide 50% solution | 2.25% | pH neutralizer |
| Polyvinyl Pyrrolidone (M.W. = 1.3 million) | 2% | thickener |
| Carboxymethyl Cellulose | 4% | thickener |
| Watermelon Flavor | 3% | flavorant |

A bead of the conditioning gel composition of Example 1 is dispensed within the inside of a tray shaped barrier layer. The tray with the conditioning gel composition is placed over the person's teeth to condition the enamel and/or exposed dentin surface in preparation for remineralization.

Example 2

A sticky, viscous conditioning gel composition is prepared by mixing together the following components:

| | | |
|---|---|---|
| Water | 22.25% | solvent/carrier |
| EDTA Disodium | 0.1% | pH buffer |
| Carbamide Peroxide | 18.5% | conditioning agent |
| Sucralose 25% solution | 0.75% | sweetener/flavorant |
| Glycerine | 41.6% | solvent/carrier |
| Carbopol 974 | 5.3% | thickener |

| | | |
|---|---|---|
| Sodium Hydroxide 50% solution | 2.25% | pH neutralizer |
| Polyvinyl Pyrrolidone (M.W. = 1.3 million) | 2% | thickener |
| Carboxymethyl Cellulose | 4% | thickener |
| Watermelon Flavor | 3% | flavorant |
| Sodium fluoride | 0.25% | remineralizing agent |

A bead of the conditioning gel composition of Example 2 is dispensed within the inside of a tray shaped barrier layer. The conditioning gel composition includes fluoride remineralizing ions. The tray with the conditioning gel composition is placed over the person's teeth to condition the enamel and/or exposed dentin surface in preparation for remineralization with a remineralization composition containing calcium ions.

Example 3

A remineralizing composition having the consistency of a rinse was formed by combining the following components:

| | | |
|---|---|---|
| Calcium Chloride | 0.2% | pH buffer |
| Sodium Phosphate Monobasic | 0.2% | pH buffer |
| Ethyl Alcohol | 20% | solvent/carrier |
| Water | 59.4% | solvent/carrier |
| Xylitol | 10% | sweetener/flavorant |
| Peppermint Oil | 2.5% | flavorant |
| Poloxamer 407 | 0.5% | surfactant |
| Methyl Paraben | 1.5% | preservative |
| Propyl Paraben | 0.2% | preservative |
| Menthol | 0.5% | flavorant |
| Calcium Phosphate Monobasic | 5% | remineralizing agent |

The rinse of Example 3 is used as a mouthwash subsequent to application of a conditioning composition such as those described in Examples 1 and 2.

Example 4

A remineralizing composition having the consistency of a rinse was formed by combining the following components:

| | | |
|---|---|---|
| Calcium Chloride | 0.4% | pH buffer |
| Sodium Phosphate Dibasic | 0.4% | pH buffer |
| Cetylpyridinium Chloride | 0.4% | preservative |
| Ethyl Alcohol | 20% | solvent/carrier |
| Water | 48.6% | solvent/carrier |
| Propylene Glycol | 20% | solvent/preservative |
| Sucralose | 0.4% | sweetener/flavorant |
| Wintermint Flavor | 2% | flavorant |
| Eucalyptus Oil | 0.3% | flavorant |
| Menthol | 0.5% | flavorant |
| Calcium Phosphate Dibasic | 7% | remineralizing agent |

The rinse of Example 4 is used as a mouthwash subsequent to application of a conditioning composition such as those described in Examples 1 and 2.

Example 5

A remineralizing composition having the consistency of a toothpaste was formed by combining the following components:

| | | |
|---|---|---|
| Water | 38.05% | solvent/carrier |
| Sident 9 | 10% | abrasive |
| Sident 22 | 8% | abrasive |
| Xylitol | 15% | sweetener/flavorant |
| Sodium Fluoride | 0.25% | remineralizing agent |
| Sodium Benzoate | 0.2% | preservative |
| Sodium Saccharine | 0.5% | sweetener/flavorant |
| Glycerine | 20% | solvent/carrier |
| Carboxymethyl Cellulose | 2% | thickener |
| Calcium Phosphate Dibasic | 5% | remineralizing agent |
| Sodium Lauryl Sulfate | 1% | surfactant |

The toothpaste of Example 5 is applied by brushing subsequent to application of a conditioning composition such as those described in Examples 1 and 2.

Example 6

A remineralizing composition having the consistency of a toothpaste was formed by combining the following components:

| | | |
|---|---|---|
| Water | 8.6% | solvent/carrier |
| Sident 9 | 15% | abrasive |
| Sident 22 | 6% | abrasive |
| Sodium Fluoride | 0.25% | remineralizing agent |
| Sodium Benzoate | 0.15% | preservative |
| Glycerine | 20% | solvent/carrier |
| Carboxymethyl Cellulose | 0.5% | thickener |
| Calcium Phosphate Dibasic | 8% | remineralizing agent |
| Sodium Lauryl Sulfate | 1.4% | surfactant |
| Sorbitol | 32% | sweetener/flavorant |
| Color | 0.3% | colorant |
| Sucralose | 0.3% | sweetener/flavorant |
| Polyethylene Glycol 400 | 4% | solvent/carrier |
| Poloxamer 407 | 1% | surfactant |
| Cool Mint Flavor | 2.5% | flavorant |

The toothpaste of Example 6 is applied by brushing subsequent to application of a conditioning composition such as those described in Examples 1 and 2.

Example 7

A remineralizing composition having the consistency of a gel was formed by combining the following components:

| | | |
|---|---|---|
| Water | 20% | solvent/carrier |
| Glycerine | 61.85% | solvent/carrier |
| Carbopol | 5% | thickener |
| Sodium Benzoate | 0.1% | preservative |
| Sodium Fluoride | 0.25% | remineralizing agent |
| Potassium Nitrate | 5% | desensitizer |
| Sodium Hydroxide | 2.4% | pH neutralizer |
| Sodium Saccharin | 0.4% | sweetener/flavorant |
| Cool Mint Flavor | 2% | flavorant |
| Calcium Phosphate Dibasic | 3% | remineralizing agent |

The remineralizing gel composition of Example 7 is applied to a barrier layer in the shape of a dental tray and is applied to the teeth subsequent to application of a conditioning composition such as those described in Examples 1 and 2.

Example 8

A remineralizing composition having the consistency of a gel was formed by combining the following components:

| | | |
|---|---|---|
| Water | 40% | solvent/carrier |
| Glycerine | 40.1% | solvent/carrier |
| Carbopol | 5% | thickener |
| Sodium Benzoate | 0.1% | preservative |
| Sodium Hydroxide | 2.4% | pH neutralizer |
| Sodium Saccharin | 0.4% | sweetener |
| Peppermint Oil | 2% | flavorant |
| Calcium Phosphate Dibasic | 10% | remineralizing agent |

The remineralizing gel composition of Example 8 is applied to a barrier layer in the shape of a dental tray and is applied to the teeth subsequent to application of a conditioning Example 9 composition such as those described in Examples 1 and 2.

Example 9

A remineralizing composition having the consistency of a chewing gum was formed by combining the following components:

| | | |
|---|---|---|
| Gum Base | 26% | carrier/thickener |
| Dextrose | 10% | sweetener/flavorant |
| Corn Syrup | 10% | sweetener/flavorant |
| Glycerine | 8% | humectant |
| Bubblegum Flavor | 4% | flavorant |
| Sucrose | 30% | sweetener/flavorant |
| Calcium Phosphate Anhydrous | 12% | remineralizing agent |

The remineralizing chewing gum composition of Example 9 is chewed so as to be applied to the teeth subsequent to application of a conditioning composition such as those described in Examples 1 and 2.

Example 10

A remineralizing composition having the consistency of a chewing gum was formed by combining the following components:

| | | |
|---|---|---|
| Wax Free Gum Base | 25% | carrier/thickener |
| Polydextrose | 12% | thickener |
| Sorbitol | 25% | sweetener/flavorant |
| Polyvinyl Acetate | 5% | carrier/thickener |
| Glycerine | 8% | humectant |
| Manitol | 8% | sweetener |
| Calcium Phosphate Anhydrous | 8% | remineralizing agent |
| Peppermint Oil | 2% | flavorant |

The remineralizing chewing gum composition of Example 10 is chewed so as to be applied to the teeth subsequent to application of a conditioning composition such as those described in Examples 1 and 2.

Example 11

A remineralizing composition having the consistency of a chewing gum was formed by combining the following components:

| | | |
|---|---|---|
| Gum Base | 25% | carrier/thickener |
| Xylitol | 40% | sweetener |
| Glycerine | 22% | humectant |
| Calcium Phosphate Anhydrous | 10% | remineralizing agent |
| Watermelon Flavor | 3% | flavorant |

The remineralizing chewing gum composition of Example 11 is chewed so as to be applied subsequent to a conditioning composition such as those described in Examples 1 and 2.

Example 12

A remineralizing composition having the consistency of a chewing gum was formed by combining the following components:

| | | |
|---|---|---|
| Gum Base | 25% | carrier/thickener |
| Xylitol | 40% | sweetener |
| Glycerine | 22% | humectant |
| Calcium Phosphate Anhydrous | 10% | remineralizing agent |
| Watermelon Flavor | 3% | flavorant |

A conditioning composition such as those described in Examples 1 and 2 is applied to the teeth so as to condition the teeth. A remineralizing gel such as those described in Examples 7 and 8 is then applied so as to remineralize the teeth. The remineralizing chewing gum composition of Example 12 is then chewed so as to complete the remineralization treatment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of conditioning and remineralizing teeth, comprising:
applying a conditioning composition to a tooth surface, the conditioning composition comprising a solvent or carrier and a conditioning agent; and
applying a remineralizing composition to the tooth surface, the remineralizing composition comprising a solvent or carrier and a remineralizing agent comprising at least one of calcium ions or fluoride ions,
wherein the conditioning composition and the remineralizing composition are applied to the tooth sequentially and without being mixed together prior to or during application to the tooth surface.

2. The method of claim 1, wherein the conditioning agent comprises a peroxide.

3. The method of claim 1, wherein the conditioning composition is acidic.

4. The method of claim 3, wherein the conditioning composition has a pH in a range of about 4 to about 7.

5. The method of claim 3, wherein the conditioning composition has a pH in a range of about 4 to about 5.

6. The method of claim 1, wherein the conditioning composition further comprises a second remineralizing agent selected from calcium ions or fluoride ions, the second remineralizing agent being different from the remineralizing agent of the remineralizing composition.

7. The method of claim 6, wherein the remineralizing agent of the remineralizing composition comprises calcium ions and the second remineralizing agent of the conditioning composition comprises fluoride ions.

8. The method of claim 1, wherein the conditioning composition is applied to the tooth surface prior to application of the remineralizing composition, the method including removing the conditioning composition from the tooth surface prior to application of the remineralizing composition.

9. The method of claim 1, wherein the remineralizing composition is applied to the tooth surface prior to application of the conditioning composition, the method including removing the remineralizing composition from the tooth surface prior to application of the conditioning composition.

10. The method of claim 1, wherein the remineralizing composition is applied to the tooth surface within about 1 hour of application of the conditioning composition.

11. The method of claim 1, wherein the remineralizing composition is applied to the tooth surface within about 30 minutes of application of the conditioning composition.

12. The method of claim 1, wherein the remineralizing composition is applied to the tooth surface within about 10 minutes of application of the conditioning composition.

13. The method of claim 1, wherein the remineralizing composition comprises a rinse and wherein applying the remineralizing composition to the tooth surface comprises rinsing the tooth surface with the remineralizing rinse composition.

14. The method of claim 1, wherein the remineralizing composition comprises a paste and wherein applying the remineralizing composition to the tooth surface comprises brushing the tooth surface with the remineralizing paste composition.

15. The method of claim 1, wherein the remineralizing composition comprises a gel and wherein applying the remineralizing composition to the tooth surface comprises placing a barrier layer including the remineralizing gel composition adjacent the tooth surface.

16. The method of claim 1, wherein the remineralizing composition comprises a chewable gum and wherein applying the remineralizing composition to the tooth surface comprises chewing the remineralizing chewable gum composition.

17. The method of claim 1, wherein the conditioning composition comprises a gel, the remineralizing composition comprises a gel, the method further comprising applying a second remineralizing composition to the tooth surface so as to remineralize the tooth surface, the second remineralizing composition being in the form of a chewable gum and that includes at least one of calcium ions or fluoride ions.

18. A method of conditioning and remineralizing teeth, comprising:
 applying a conditioning composition to a tooth surface, the conditioning composition comprising a solvent or carrier and a peroxide conditioning agent;
 removing the conditioning composition from the tooth surface; and
 applying a remineralizing composition to the tooth surface after removing the conditioning composition, the remineralizing composition comprising a solvent or carrier and a remineralizing agent comprising at least one of calcium ions or fluoride ions.

19. The method of claim 18, wherein the conditioning composition is applied to the tooth surface for a time period of at least 10 minutes and wherein the remineralizing composition is thereafter applied to the tooth surface for a time period of at least 10 minutes.

20. A method of conditioning and remineralizing enamel and/or exposed dentin, comprising:
 applying a conditioning composition to one or more teeth so as to temporarily weaken and form a conditioned tooth surface, the conditioning composition comprising a solvent or carrier, a peroxide conditioning agent, and fluoride ions; and
 applying a remineralizing composition to the conditioned tooth surface, the remineralizing composition comprising a solvent or carrier and calcium ions,
 wherein the conditioning composition and the remineralizing composition are applied to the one or more teeth sequentially and without being mixed together prior to or during application to the one or more teeth.

* * * * *